United States Patent [19]

Diderichsen

[11] Patent Number: 4,920,048

[45] Date of Patent: Apr. 24, 1990

[54] METHOD FOR STABILIZING EXTRA-CHROMOSOMAL ELEMENTS IN BACTERIA DURING CULTIVATION

[75] Inventor: Borge K. Diderichsen, Hellerup, Denmark

[73] Assignee: Novo Industri A/S, Denmark

[21] Appl. No.: 807,483

[22] Filed: Dec. 10, 1985

[30] Foreign Application Priority Data

Dec. 12, 1984 [DK] Denmark ............................ 5940/85

[51] Int. Cl.$^5$ ...................... C12P 21/00; C12N 15/00; C12N 9/90; C12N 1/20
[52] U.S. Cl. .................................. 435/69.1; 435/223; 435/233; 435/252.31; 435/252.33; 435/320; 435/69.4
[58] Field of Search ................ 435/68, 91, 172.3, 233, 435/170, 252.3, 320, 259, 822, 832, 848; 935/29, 73, 71, 55, 60

[56] References Cited

FOREIGN PATENT DOCUMENTS

| | | |
|---|---|---|
| 0012494 | 6/1980 | European Pat. Off. . |
| 0049619 | 2/1981 | European Pat. Off. . |
| 0080848 | 8/1983 | European Pat. Off. . |
| 0120629 | 3/1984 | European Pat. Off. . |
| 0106542 | 4/1984 | European Pat. Off. . |
| 0127328 | 4/1984 | European Pat. Off. . |

OTHER PUBLICATIONS

Alberts et al., 1983, Molecular Biology of the Cell Garland Publ., Inc., N.Y.
Palva et al., 1981, Gene 15:43–51.
Wasserman et al., 1983, J. Bacteriol. 153(3): 1439–1450.
Buxton et al., 1980, J. Gen. Microbiol. 120: 283–293.
Yang et al., 1984, J. Bacteriol. 160(1): 15–21.
Freese et al., Proc. Nat'l. Sci. USA 51: 1164–72 (1964).
Dul et al., J. Bacteriol. 15: 1212–14 (1973).
Spizizen, Proc. Nat'l. Acad. Sci. 44: 1072–78 (1958).
Wijsman, Genet. Res., Camb. 20: 269–77 (1972).
Vieria et al., Gene 19: 259–68 (1982).
Bolivar et al., Gene 2: 95–113 (1977).
Gryczan et al., J. Bacteriol. 134: 318–29 (1978).
Gryczan et al., J. Bacteriol. 141: 246–53 (1980).
Yasbin et al., J. Bacteriol. 121: 296–304 (1975).
Wild et al., Molec. Gen. Genet. 198: 315–22 (1985).
Ferrari et al., Biotech. 3: 1003–1007 (1985).
Bio/Technology, vol. 3, Nov. 1985, "Isolation of an Alanine Racemase Gene from Bacillus subtilis and its Use for Plasmid Maintenance in B. subtilis", Ferrari et al.

Primary Examiner—Jayme A. Huleatt
Assistant Examiner—Richard C. Peet
Attorney, Agent, or Firm—Saidman, Sterne, Kessler & Goldstein

[57] ABSTRACT

A method for stabilization of extra-chromosomal elements in bacteria during cultivation which comprises transformation of a host bacterium having a defect in a chromosomal gene needed for the synthesis or maintenance of the cell envelope with an extra-chromosomal element capable of complementing the chromosomal gene defect of the host bacterium, the extra-chromosomal element also including an expressible DNA-sequence coding for a desired product.

10 Claims, 6 Drawing Sheets

METHOD FOR STABILIZING EXTRA-CHROMOSOMAL ELEMENTS IN BACTERIA DURING CULTIVATION

BACKGROUND OF THE INVENTION

1. Field of the Invention

This invention relates to a novel method for stabilizing extra-chromosomal elements in bacteria during cultivation, without the need for addition of antibiotics or other undesirable components to the growth medium, with the purpose of increasing the yield or quality of fermentation products.

2. Description Of The Background Art

Microorganisms harboring extra-chromosomal genetic elements, for example plasmids, are, generally speaking, unstable in the sense that the element may frequently be irreversibly lost. This instability is particularly pronounced if the plasmid is not endogenous to the host microorganism, for instance, because it comprises genes from other organisms or has been constructed by gene splicing.

To increase plasmid stability, an antibiotic or another bioactive compound to which the plasmid but not the chromosome confers resistance, is commonly added to the medium used for cultivation of the microorganism. In such a medium only those cells retaining the plasmid with the antibiotic resistance gene proliferate. The major disadvantages of this approach are that it requires large scale growth of antibiotic resistant microorganisms, addition of expensive antibiotics to the growth medium with possible adverse effects on the environment, and subsequent extensive purification to remove the antibiotic from the desired product.

Complementation of an auxotrophic mutation of the host chromosome is another known method for stabilization of plasmids. This approach, however, seriously restricts the composition of the growth medium and requires cultivation in a growth medium that does not contain the nutrient required by the host microorganism, thereby limiting the options available for improving productivity.

The object of the present invention is to provide a method for stabilization of extra-chromosomal elements in transformed bacteria, without the necessity of using antibiotics and without severe restrictions on the composition of the growth media.

It is another object of the present invention to provide stabilized extra-chromosomal elements and transformed bacteria containing such stabilized extra-chromosomal elements.

It is a further object of the present invention to provide a method for producing desirable products in transformed bacteria without the necessity of using antibiotics or special restrictions on the composition of the growth media.

Other objects of the invention will become apparent to those skilled in the art to which it pertains.

SUMMARY OF THE INVENTION

The invention resides in the discovery that extra-chromosomal elements can be maintained in host bacteria during cultivation in a given ordinary media if the extra-chromosomal elements code for a certain function which, under the given conditions, is required for normal growth of the host.

When transforming a host bacterium having a mutation, deletion or another defect in a gene encoding a function which, under the given conditions, is required for normal growth of the host with, for instance, a plasmid containing a gene encoding this function, only those cells transformed with and maintaining the plasmid will survive. This is the case because only in such cells is the requirement of the host cells supplemented by the plasmid. However, permanent plasmid maintenance is only assured if transfer of genetic information from plasmid to chromosome cannot take place, and the rate of spontaneous mutation of the host bacteria into a mutant with no such requirement is insignificant.

According to a first aspect of the present invention there is provided a method for stabilizing extra-chromosomal elements in bacteria during cultivation, said method comprising:

providing an extra-chromosomal element containing a DNA-sequence coding for a structural or functional component which is needed for the synthesis or maintenance of the bacterial cell envelope; and transforming a bacterial host having a defect in the chromosomal gene for said structural or functional component, with the extra-chromosomal element containing said DNA-sequence;

whereby the extra-chromosomal element suppresses the requirement caused by the chromosomal gene defect of the host bacterium and loss of the extra-chromosomal element during cultivation is insignificant.

The method furthermore includes construction of a host bacterium from which suppression or elimination of the chromosomal defect by spontaneous mutation is insignificant. The invention also includes construction of an extra-chromosomal element from which the DNA-sequence suppressing the requirement caused by the chromosomal defect of the host bacterium cannot be transferred to the chromosome of the host separately from the rest of the extrachromosomal element.

According to a further aspect of the present invention there is provided a transformed bacterium having a defect in a chromosomal gene needed for the synthesis or maintenance of the bacterial cell envelope, said transformed bacterium containing an extra-chromosomal element capable of suppressing the requirement caused by the chromosomal gene defect of the host bacterium.

The present invention furthermore provides a method for producing a desired product in transformed bacteria, (i.e. DNA, RNA, peptides, and proteins) which comprises:

providing a combined extra-chromosomal element containing (i) a DNA-sequence coding for a structural or functional component which is needed for the synthesis or maintenance of the bacterial cell envelope, and (ii) a gene coding for said desired product;

transforming a bacterial host having a defect in the chromosomal gene for said structural or functional component with said combined extra-chromosomal element;

cultivating the transformed bacterium in a suitable nutrient medium; and recovering the desired product from the culture medium.

The present invention also comprises a method for the production of a desired product in transformed bacteria which comprises:

cultivating in a suitable nutrient medium bacteria having a defect in a chromosomal gene needed for the synthesis or maintenance of the bacterial cell envelope, said bacteria containing a combined extra-chromsomal element capable of suppressing the requirement caused by the chromosomal gene defect of the host bacterium, said plasmid also containing a DNA-sequence coding for said desired product; and recovering the desired product from the culture medium.

DESCRIPTION OF THE DRAWINGS

The invention will be further described with reference to the accompanying drawings in which.

DESCRIPTION OF THE PREFERRED EMBODIMENTS

Figure 1:
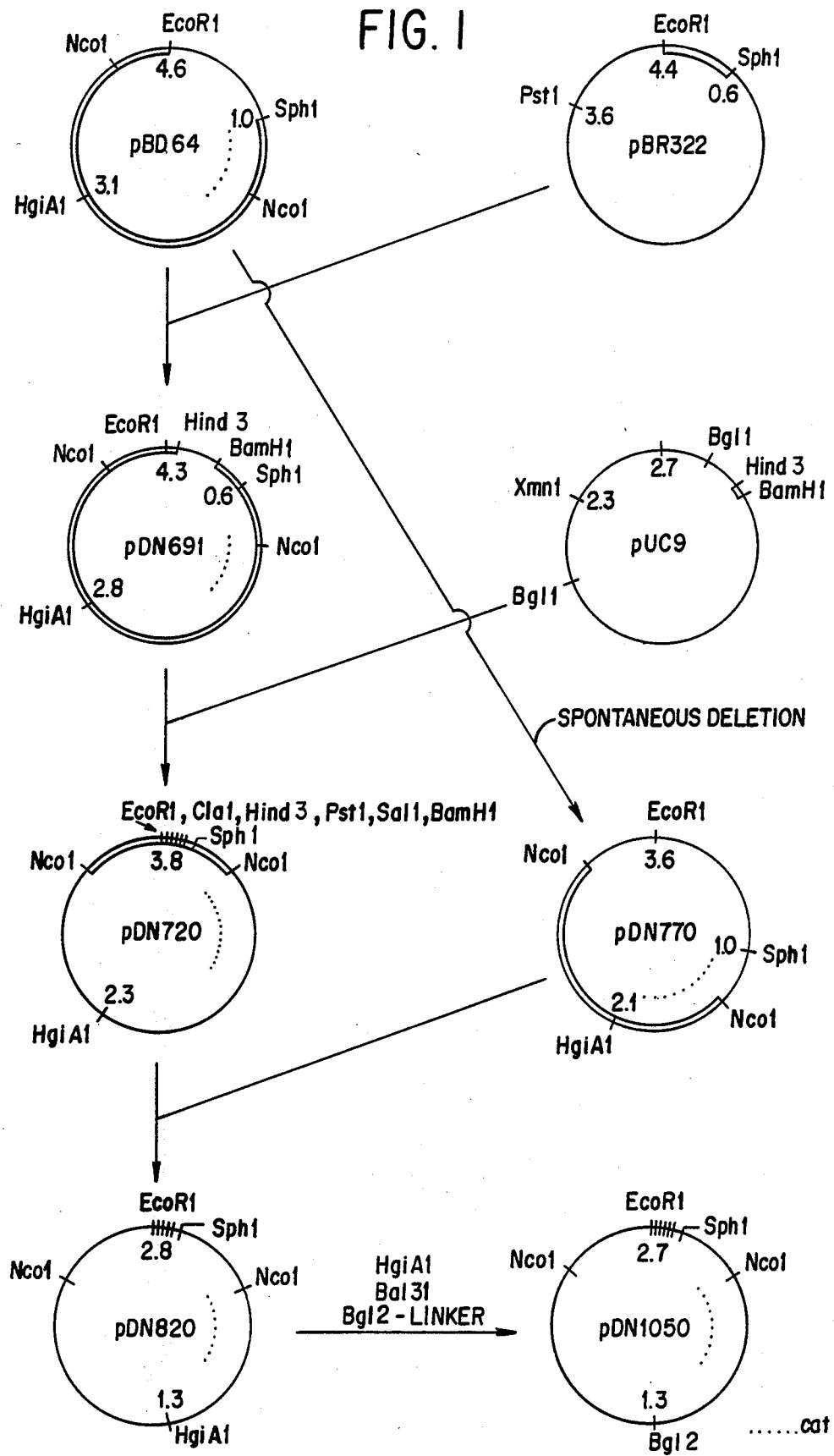
FIG. 1 illustrates the construction of plasmids pDN691, pDN770, pDN820, and pDN1050.

In the description and claims, the following terms are employed:

dal gene: the gene for D,L-alanine racemase.

dal+ gene: a functional gene (wild type) for D,L-alanine racemase.

dal-1 gene: a gene with a mutation in the D,L-alanine racemase gene normally causing requirement for external D-alanine.

dal− host: a host having a mutation in the dal gene (herein normally requiring external supply of D-alanine for growth).

dal+ host: a host with a wild type dal gene.

Dal+ host: a host without requirement for external D-alanine.

Dal− host: a host with requirement for external D-alanine.

Cam$^R$: chloramphenicol resistance.

Kan$^R$: kanamycin resistance.

Amp$^R$: ampicillin resistance.

bla: gene for beta-lactamase causing Amp$^R$.

cat: gene for chloramphenicol acetyl transferase causing Cam$^R$.

amyM: gene for a maltogenic amylase.

The extra-chromosomal element used in the invention complements the chromosomal gene defect of the host. In other words, the function which is absent from the host due to the gene defect is made up by the genetic information coding for that function, present in the extra-chromosomal element.

As used herein the term "extra-chromosomal element" means a plasmid, bacteriophage or any genetic material which is not normally present in the host bacteria either as an independent molecule or as integrated into the chromosome. Preferred extra-chromosomal elements are plasmids, although bacteriophages and other vector systems can also be used.

In addition, it should be understood that an extra-chromosomal element may after transformation become integrated into the chromosome. Such "integrated extra-chromosomal elements" are also part of the invention.

Suitable host bacteria are bacteria belonging to the Bacillus or Enterobacteriaceae species, e.g. *Bacillus subtilis* and *Escherichia coli*, although use of other suitable bacteria may be evident to those skilled in the art.

For most bacteria, the ability to grow and divide depends on a well sustained cell envelope (i.e. cell membrane, cell wall and related structures). Disruption or disintegration of the envelope usually leads to lysis or cessation of growth.

One of the components indispensable for a stable cell envelope in *Bacillus subtilis* and most other bacteria is D-alanine. D-alanine is an essential part of the cell wall where it serves to crosslink polysaccharide chains, thus conferring the cell with the necessary rigidity. D-alanine is not present in most conventional growth media, and normally many bacteria including *B. subtilis* and *E. coli* synthesize this amino acid from L-alanine by means of the enzyme D,L-alanine racemase, and do not require an external source of D-alanine for growth. Some mutants need an external supply of D-alanine for growth, as for instance dal-1 mutants of *B. subtilis* in which the D,L-alanine racemase gene has been damaged due to the mutation (Freese et al., *Proc. Natl. Acad. Sci. U.S.A.* 51:1164–72, 1964, Dul et al, *J. Bacteriol.* 15:1212–14, 1973). Other mutants may require an external supply of other metabolites for maintenance of the cell envelope, as for instance diaminopimelic acid, D-glutamic acid, and N-acetylglucosamine.

According to the present invention it has been proven that plasmids containing a functional gene for a D,L-alanine racemase assure their maintenance in dal− host if the dal+ gene cannot be transferred from plasmid to chromosome, if the frequency of spontaneous mutation of the host to a Dal+ phenotype is insignificant, and if external D-alamine is not available to the cell.

Thus by inserting a gene for a desired product in an appropriate dal+ plasmid, and culturing the plasmid in an appropriate dal− host, the dal+ plasmid will be maintained in the cell population during growth, ensuring high yields of the desired product being expressed during the autonomous replication of the plasmid. As D-alanine is absent in many conventional growth media, no further restrictions are needed to be applied on these media.

Accordingly, the present invention represents a convenient method for stabilizing extra-chromosomal elements carrying expressible genes for desired products during cultivation.

To ensure that the rate of spontaneous mutation of the host to a Dal+ phenotype is insignificant, it may, in some instances, be necessary to delete a part of the dal gene.

However, by combination of such host containing a deletion of a part of the dal gene necessary for expression of the Dal+ phenotype with a dal+ plasmid harbouring the entire dal+ gene and segments homologous to the DNA that flanks both sides of the deletion on the chromosome, transfer of the dal+ allele from plasmid to chromosome may still take place by homologous crossover. To avoid such homologous crossover a host can be constructed in which the dal deletion extends into the segments immediately flanking the dal gene on the chromosome.

Also a plasmid can be constructed which comprises a functional dal+ gene but not DNA homologous to the DNA that flanks both sides of the gene deletion on the chromosome. Combination of this latter plasmid with aforementioned dal− hosts constitutes a preferred host-vector pair.

Alternatively, dal+ allele transfer may be prevented either by using a recombination deficient host, or by using an extra-chromosomal dal+ gene with no or little DNA-homology with the chromosome of the host bacterium.

The dal+ gene is preferably derived from a *B. subtilis* strain as explained in further detail below. Besides the dal+ gene, the extra-chromosomal element should also include elements for replication, e.g. the replication functions from the high-copy plasmid pUB110 for replication in Bacillae or other gram positive bacteria, or the replication function of pBR322 for replication in Enterobacteriaceae or other gram-negative bacteria.

Production of a desirable product according to the present invention is illustrated by production of a maltogenic amylase from a Bacillus strain (NCIB 11837) expressed by its own promoter. Other examples of desired products which may be produced according to the present invention are other kinds of amylases, amyloglycosidases, pullulanases, proteinases, lipases, hormones, and other enzymes or eukaryotic proteins and peptides.

The method of the invention allows the cultivation of transformed bacteria in antibiotic-free media. It should be understood, however, that such is not a condition for operability of the invention, only a consequence thereof. If it becomes useful or preferable to cultivate the transformed bacteria of the invention in the presence of antibiotic(s), it can, of course be done.

A specific embodiment within the invention is the preparation of dal− hosts complemented with the dal+ gene present in an extra-chromosomal element.

The dal+ gene was obtained from DN497, a derivative of *Bacillus subtilis* 168 (Spizizen, *Proc. Natl. Acad. Sci.* 44, 1072–78, 1958). Chromosomal DNA was completely digested with appropriate restriction enzymes and ligated with plasmid pDN691 conferring resistance to chloramphenicol and kanamycin, and capable of replicating in *B. subtilis*. The ligated DNA was transformed into a D-alanine requiring *B. subtilis* dal-1 selecting complementation of the D-alanine requirement. A Dal+ transformant which had concomitantly become $Cam^R$ (chloramphenicol resistant) contained a recombinant plasmid derived from pDN691 on which the Dal+ and $Cam^R$ phenotypes were linked. Possibly due to homologous recombination between chromosome and plasmid only minute amounts of plasmid could be detected in the transformant.

To avoid recombination and subsequent integration of plasmid into the chromosome, plasmid was prepared from this Dal+ and $Cam^R$ transformant and transformed into a D-alanine requiring and recombination deficient strain DN733 dal− recE− selecting for Dal+. The transformants concomitantly became Dal+ $Cam^R$ and $Kan^R$ (kanamycin resistant).

The transformants contained small amounts of a plasmid of about 16kb. From this plasmid, a 2.0 kb ClaI-SphI fragment conferring a Dal+ phenotype was cloned on a 2.6 kb fragment on plasmid pDN820: $Cam^R$ in strain DN608: dal− selecting for $Cam^R$ Dal+ to give a recombinant plasmid pDN1000 of 4.6 kb. This plasmid could, however, replace the dal-1 mutation on the chromosome of recombination proficient strains (e.g. DN608) with the dal+ allele by homologous recombination. The selection of a Dal+ phenotype without concomitant $Cam^R$ selection would, however, no longer assure maintenance of the plasmid upon recombination.

To prevent transfer of the dal+ allele to the chromosome by homologous recombination and subsequent loss of plasmid, and to reduce the frequency of mutations causing a Dal+ phenotype, a deletion of both the dal gene in the host and a neighboring segment was made in the host chromosome. The cloned dal gene was cut with restriction enzymes EcoR1 and EcoR5 and subsequently digested with exonuclease Ba131. The digestion mixture was ligated and transformed into DN608 dal−, selecting for $Cam^R$. Transformants containing plasmids with deletions in the dal gene were identified as Dal− $Cam^R$. To construct a host strain with the appropriate deletion in the dal gene, a dal+ host was transformed with one of the plasmids, pDN1274 $Cam^R$ dal−. Selecting for $Cam^R$, about 0.1% of the transformants were Dal−, presumably due to the replacement of the chromosomal dal+ gene with the dal− deletion from pDN1274 by homologous recombination. Following spontaneous loss of pDN1274 upon growth in the presence of D-alanine and absence of chloramphenicol, the plasmid free strain DN1280 remained Dal−. Southern blotting analysis of chromosomal DNA from DN1280 showed that it indeed harboured the expected dal deletion. This dal− deletion host, strain DN1280, was transformed with a dal+ plasmid (e.g. pDN1090) harbouring both the entire dal+ gene and segments homologous to the DNA flanking both sides of the deletion on the chromosome. Transfer of the dal+ gene from plasmid to chromosome by homologous recombination could therefore take place and the host could be converted into dal+. Hence, maintenance of the plasmid was no longer a condition for a Dal+ phenotype and the plasmid was frequently lost. A dal+ plasmid, pDN1277, was then constructed harbouring the entire functional dal+ gene, but not DNA homologous to the DNA that flanks the deletion on the host chromosome as explained above. Therefore, transfer of dal+ from plasmid to chromosome by homologous recombination could not take place upon transformation of the dal− deletion host with pDN1277. Hence, DN1280 is a suitable dal− host in D-alanine free media for dal+ plasmids which do not harbour the DNA including the EcoR5 site which normally flanks the dal gene on the chromosome but which has been deleted in DN1280.

In order to ascertain that cloned genes of scientific or commercial interest indeed could be maintained on plasmids in D-alanine free media by the above host-vector system, the gene for the maltogenic amylase from Bacillus C599 (NCIB 11837) was transferred to a dal+ plasmid. Two plasmids pDN1130 and pDN1290 were constructed. Both plasmids harbour the replication functions of plasmid pUB110 and functional dal and amyM genes. Neither plasmids confer resistance to any antibiotic. Plasmids pDN1130 and pDN1290 were transformed into the above *B. subtilis* strain DN1280. Strain DN1280 harbours as mentioned above a chromosomal deletion which includes both a part of the dal gene necessary for expression of the $Dal^{30}$ phenotype and an adjoining segment which is not required for the Dal+ phenotype whether it be part of the dal gene senso strictu or not. This latter part of the deletion is not harboured by pDN1290. Accordingly, the dal+ gene cannot be transferred from pDN1290 to the chromosome by double homologous recombination. Plasmid pDN1130, on the other hand, harbours both the entire segment which is deleted on the chromosome and adjoining segments. For this reason transfer of the dal+ gene from plasmid to chromosome and subsequent plasmid loss may take place.

The obtained transformed strains DN1297 (=DN1280 pDN1130) and DN1300 (=DN1280 pDN1290) were tested for plasmid stability during cultivation (see example 7). When culturing DN1297 homologous crossover restoring the dal+ gene on the chromosome took place and both the plasmid and the Amy− phenotype were frequently lost.

When culturing DN1300 no loss of the Amy+ phenotype conferred by the plasmid was observed upon growth in media without D-alanine. If D-alanine was added to the medium, however, cells frequently lost the plasmid and became Amy−Dal−. Thus, stable maintenance of a plasmid harbouring a non-endogenous gene of commercial interest, in an antibiotic-free medium was demonstrated.

To demonstrate that plasmids may be maintained also in gram-negative organisms by suppression of a D-alanine requirement the dal gene of *B. subtilis* was cloned on a plasmid in a D-alanine requiring *Escherichia coli* mutant and shown to complement the requirement.

Further details of the present invention will appear from the following examples.

EXPERIMENTAL PART

Preparation of plasmids and chromosomal DNA and transformation of *Bacillus subtilis* and *E. coli* were conducted according to the following general procedures. Digestion with restriction enzymes, Bal 31 nuclease treatment, oligo-DNA-linker insertion and ligation with T4-ligase of DNA were performed with enzymes from New England Biolabs under the conditions suggested by the supplier.

Strains

All *Bacillus subtilis* strains were derivatives of *Bacillus subtilis* 168 (Spizizen, *Proc.Natl.Acad.Sci.* 44: 1072–78, 1958). RUB200: aroI906, amyE07, amyR2 was obtained from Dr. Frank Young, University of Rochester, N.Y. SL438:trpC2 (sporulation and protease deficient) was obtained from Dr. Kim Hardy, Biogen, Geneva. DN497: amyE07, amyR2 is an aro+ transformant of RUB200 with chromosomal DNA from SL438. QB1133: aroI906, metB5, sacA321, amyE was from Dr. Georges Rapoport, IRBM, Paris. QB1130:dal, metB5, sacA331, amyE was obtained from the Bacillus Genetic Stock Center, Columbus, Ohio. DN608: dal-1, metB, sacA, amyE was an aro+, dal-1 transformant of QB1133 with chromosomal DNA from QB1130. MT120: leuB6, recE4 $r_m^- m_m^-$ was obtained from Dr. Teruo Tanaka, Mitsubishi-Kasei Institute of Life Sciences, Toyko. DN773: dal-1, amyE, recE, sacA was a met+ recE transformant of DN608 with chromosomal DNA from MT120. DN606 is DN608 transformed with plasmid pUB110.

*Escherichia coli* strain TKL10: thr-1 leuB6 codAl trp-64 pyrF101his-108 thyA6 argG66 ilvA634 thi-1 alr-1 deoCl lacrl tonA21tsx95 supE44 (Wijsman, Genet. Res., Camb. 20: 269–77, 1972) was obtained from Dr. Barbara Bachmann at the *E. coli* Genetic Stock Center Connecticut, U.S.A. (CGSC 5466).

Plasmids pUC9 of 2.7 kb confers resistance to ampicillin and was derived from pBR322 (Vieira et al., Gene 19: 259–68, 1982). pBR322 of 4.4 kb confers resistance to ampicillin and tetracycline (Bolivar et al., Gene -2:95–113, 1977).

Plasmids pUB110 and pBD64 (Gryczan et al., *J. Bacteriol.* 134: 318–329, 1978, and Gryczan et al., *J. Bacteriol.* 141: 246–53, 1980) were isolated from *B. subtilis* strains BD366 and BD624, respectively. pUB110 and pBD64 both confer resistance to kanamycin and pBD64 also to chloramphenicol. *B. subtilis* strains BD366 and BD624 can be obtained from the Bacillus Genetic Stock Center, Columbus, Ohio, U.S.A. (strain file number BGSC 1E6 and 1E22). Plasmid pDN452 of 7.6 kb confers resistance to chloramphenicol and kanamycin and harbours the structural gene for a maltogenic amylase from *Bacillus subtilis* NCIB 11837. The construction of pDN452 is described in EP patent application No. 84301994.4.

I. Transformation of *B. subtilis*

Competent *Bacillus subtilis* cells were prepared according to Yasbin et al. (*J. Bacteriol.* 121: 296–304, 1975). Cells were then harvested by centrifugation (7000 rpm, 3 min.), resuspended in one tenth volume of supernatant including 20% glycerol, frozen in liquid nitrogen and stored at −70° C. For transformation, frozen cells were thawed at 42° C. and mixed with one volume buffer (Spizizen's minimal medium (Spizizen, *Proc. Natl. Acad. Sci. USA* 44:1072–78, 1958)) with 0.4% glucose, 0.04M MgCl$_2$ and 0.002M EGTA). DNA was added and the mixture incubated with shaking at 37° C. for 20 min. Cells were then plated on appropriate selective media.

II. Transformation of *E. coli*

An overnight culture of *E. coli* K-12 strain No. 802 in LB (10 g Bacto tryptone, 5 g Bacto yeast extract and 10 g NaCl per liter water, pH 7.0) was diluted 100 fold in 500 ml LB and grown at 37° C. to OD$_{450}$ =0.4. The culture was chilled, left 15 min. on ice, spun for 15 min. at 3000 rpm (in a Sorvall GS3 rotor), resuspended in 200 ml cold 0.1M CaCl$_2$, left on ice for 20 min., spun for 10 min. at 3000 rpm, resuspended in 5 ml cold 0.1M CaCl$_2$ and left on ice for 20 hours. Cold glycerol was then added to 10% and aliquotes were frozen liquid nitrogen and stored at −70° C. Frozen cells were thawed on ice, DNA was added, the mixture incubated 45 min. on ice, 2 min. at 37° C. and then plated on an appropriate selective medium.

III. Preparation

*E. coli* was grown overnight in 250 ml LB, 0.4% glucose and an appropriate antibiotic. Cells were harvested by centrifugation and resuspended in 4 ml Buffer 1 (0.025M Tris.HCl, pH =8.0, 0.01M EDTA, 0.05M glucose, 2 mg/ml lysozyme). The suspension was incubated at 0° C. for 15 min. and then mixed with 8 ml Buffer 2 (0.2M NaOH, 1% SDS). Then 6 ml Buffer 3 (3M NaAcetate, pH 4.8) was added, the mixture kept at 0° C. for 60 min. followed by centrifugation for 20 min. at 19000 rpm (ca. 45000 g in Sorvall SS34 rotor). The supernatant was precipitated with 0.6 vol. cold isopropanol and resuspended in 1.2 ml 5TE (0.05M Tris.HCl, pH =8.0, 0.005M EDTA), plus 20 ul boiled RNase A (Boehringer) (2 mg/ml). 30 min. later the solution was layered on top of 4.0 ml Buffer 4 (80 g CsCl plus 56 ml 5TE) and 0.1 ml EtBr (10 mg/ml ethidium bromide) in a VTi65 tube. The mixture was centrifuged at 45000 rpm for 20 h. The plasmid was then removed from the tube, dialyzed and extracted as described in Section VI.

IV. Preparation of plasmids from B. subtilis

Plasmid was prepared as described for E. coli strains (see section III) but with the following modifications. Growth was in LB including 0.01M potassium phosphate, pH = 7.0 and an appropriate antibiotic (e.g. 6 ug/ml chloramphenicol) and if required 100 ug/ml D-alanine. After harvest, cells were incubated at 37° C. with lysozyme. Buffer 2 was replaced by a mixture of one volume Buffer 2 and three volumes Buffer 5 (0.2M glycine, 0.2M NaCl and 1% SDS). The following steps were the same as in III.

V. Small scale preparation of plasmids from B. subtilis

Plasmid from 5 ml B. subtilis in LB (including 0.01 M phosphate pH = 7.0 and appropriate antibiotics and D-alanine if required) was prepared as in section IV except: 1: volumes of buffers were reduced four fold. 2: 0.5 ml phenol and 0.5 ml chloroform are added after Buffer 3. 3: After centrifugation at 19000 rpm, the supernatant was precipitated with ethanol, resuspended in 400 ul Buffer 6 (0.05M Tris.HCl pH = 8.0, 0.1M NaAcetate), the plasmid was again precipitated, resuspended in 400 ul Buffer 6, precipitated, washed and resuspended in 100 ul TE (0.01M Tris.HCl, pH = 8.0, 0.001M EDTA) with 1 ug/ml boiled RNase A (Boehringer).

VI. Preparation of chromosomal DNA from B. subtilis

A pellet of frozen cells from about 50 ml culture was resuspended in 1.1 ml Buffer (0.05 M Tris.HCl, pH = 7.4, 0.1M NaCl, 25% sucrose). 100 ul lysozyme (25 mg/ml) and 150 ul EDTA (0.5M, pH = 8.0) were added. The mixture was incubated at 37° C. for 30 min. 2 ml 0.2% SDS was added followed by incubation for 30 min. at 37° C. 1 g CsCl and 0.05 ml EtBr (10 mg/ml) were added per 0.95 ml mixture and the mixture was centrifuged at 45000 rpm, 15° C., for 20 hours in a VTi65 rotor (Beckman).

The DNA was located under a long wave UV lamp and removed by puncturing the tube with a syringe. EtBr was extracted with isopropanol and the solution dialyzed for 2 hours against TEE (0.01M Tris.HCl, pH = 8.0, 0.01M EDTA). The solution was then adjusted to 8 ml with TEE and extracted twice with phenol and once with chloroform. The DNA was precipitated with 0.1 M NaCl and cold ethanol, and dissolved in 1 ml TE (0.01M Tris.HCl, pH = 8.0, 0.001M EDTA). The solution of chromosomal DNA was kept at 4° C.

Example 1

Construction of plasmid pDN1050 (FIG. 1)

Plasmid pBD64 was cut with restriction enzymes EcoR1 and Sph1 and a 3.6 kb fragment was ligated with a 0.56 kb EcoR1-Sph1 fragment from E. coli plasmid pBR322. The resulting plasmid pDN691 of 4.2 kb confers chloramphenicol and kanamycin resistance. A 0.4 kb Hind3-BamHl fragment of pDN691 was replaced with a 0.02 kb Hind3-BamHl fragment of E. coli plasmid pUC9. The resulting plasmid pDN720 of 3.8 kb confers chloramphenicol and kanamycin resistance.

A 2.8 kb Ncol-Ncol fragment of pDN720 was replaced with a 1.8 kb Ncol-Ncol fragment of pDN770. pDN770 of 3.6 kb was a spontaneous deletion of pBD64 and confers chloramphenicol resistance. The resulting plasmid pDN820 of 2.8 kb confers chloramphenicol resistance. pDN820 was opened at the single HgiAl site and digested with Bal31 for 30 sec. at 30° C. whereby a fragment of 0.1 kb was removed. The obtained linear fragments were ligated with a Bgl2 oligonucleotide linker from New England Nuclear (No. 1001). Plasmid pDN1050 of 2.7 kb including one Bg12 linker and conferring chloramphenicol resistance was isolated from this ligation mixture.

EXAMPLE 2

Figure 2:
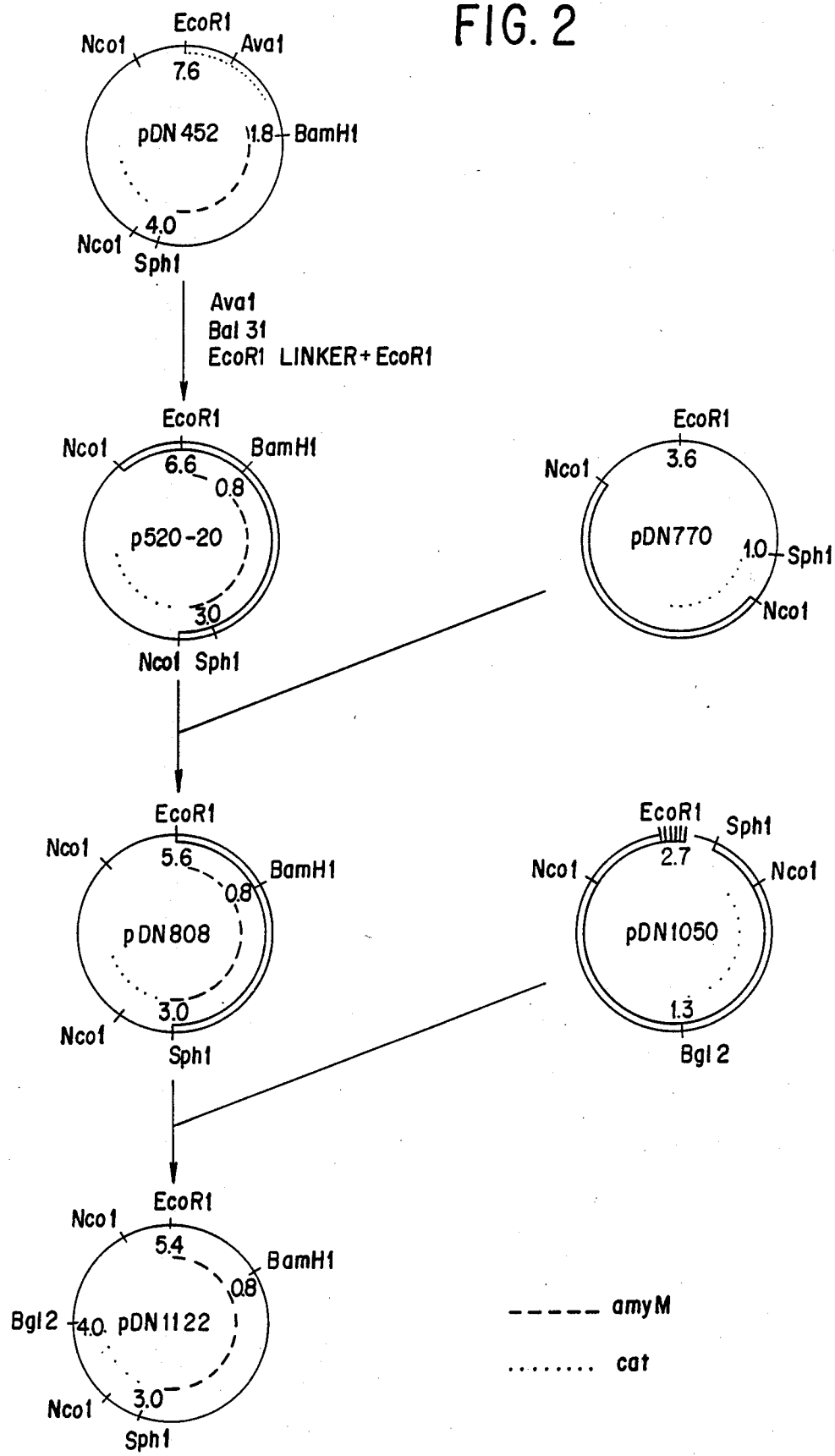
FIG. 2 illustrates the construction of pDN1122.

Construction of plasmid pDN1122 (FIG. 2)

Plasmid pDN452 of 7.6 kb conferring resistance to chloramphenicol and kanamycin and harbouring the structural gene amyM for a maltogenic amylase of Bacillus C599 was digested with Aval, treated with exonuclease Bal31, ligated with EcoR1 oligonucleotide linker (Biolabs No. 1004), digested with EcoR1, ligated with T4-ligase and transformed into B. subtilis DN497:amyE selecting for Cam$^R$. One Amy$^+$ transformant contained plasmid p520-20 of 6.6 kb. The amylase yield of p520-20 was not less than the yield of pDN452.

A 2.7 kb Ncol-Ncol fragment of p520-20 was then replaced with a 1.7 kb Ncol-Ncol fragment of pDN770 (prepared as in Example 1). The obtained plasmid pDN808 of 5.6 kb harbours amyM and confers resistance to chloramphenicol.

A 2.6 kb EcoR1-Sph1 fragment of pDN808 was replaced with a 2.4 EcoR1-Sph1 fragment of pDN1050 (prepared in Example 1). The resulting plasmid pDN1122 of 5.4 kb harbours amyM and confers resistance to chloramphenicol.

EXAMPLE 3

Cloning of the dal gene

About 3 ug chromosomal DNA from B. subtilis strain DN497 and 1 ug plasmid pDN691 Cam$^R$ Kan$^R$ were completely digested with restriction enzymes BamH1 and Sph1. Chromosomal and plasmid DNA were mixed and ligated with T4-ligase and transformed into strain DN606:dal$^-$ pUB110:Kan$^R$ Among about 200 Dal$^+$ transformants, one had concomitantly become Cam$^R$ as a suggestion that the Dal$^+$ phenotype was linked to a recombinant plasmid derived from pDN691. Plasmids were prepared from this Dal$^+$ Cam$^R$ transformant and transformed into strain DN773 dal$^-$ recE$^-$ selecting for Dal$^+$Dal$^+$transformants concomitantly became Cam$^R$ and Kan$^R$. The transformants contained only very small amounts of a plasmid of about 16 kb.

From this plasmid a 2.0 kb Cla1-Sph1 fragment conferring a Dal$^+$ phenotype was cloned in the Cla1 and Sph1 sites of plasmid pDN820 in strain DN608:dal$^-$ to give a recombinant plasmid, pDN1000 of 4.6 kb.

Figure 3:
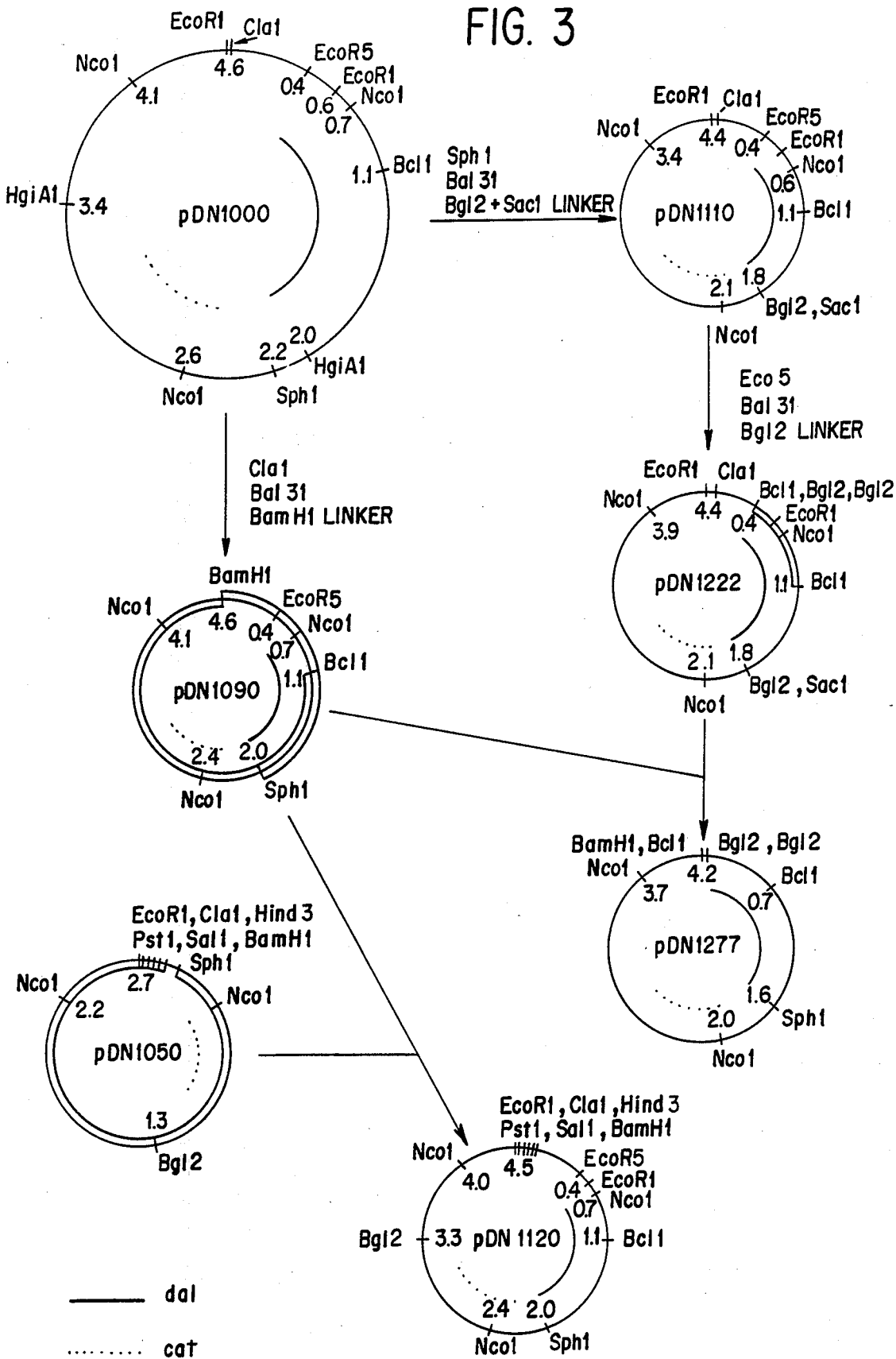
FIG. 3 illustrates the construction of plasmids pDN1090, pDN1120, pDN1222, and pDN1277 and a map of restriction enzyme sites on pDN1000.

A map of restriction enzyme sites on pDN1000 is given in FIG. 3. The transformed strain DN1000=DN608 pDN1000 was deposited with the National Collection of Industrial Bacteria, (NCIB), Torry Research Station, Aberdeen, Scotland, on Dec., 7, 1984 and accorded the reference number NCIB 12029. NCIB being an international depository authorized under the Budapest Treaty of 1977, affords permanence of the deposit and accessibility thereto by the public in accordance with Rules 9 and 11, respectively, of the above treaty.

The following observations ascertained that the cloned chromosomal fragment indeed included the dal gene (as defined by the dal-1 mutation) and not another gene being able to suppress the D-alanine requirement:

1: Linearized (non-replicative) plasmid transformed a dal⁻ recipient to Dal⁺ but not to $Cam^R$ as an indication of homologous recombination between the dal gene of the chromosome and the cloned chromosomal fragment.

2: About 0.2% of plasmids prepared from a host bacterium being dal-1 on the chromosome were dal⁻ (yet with a restriction enzyme pattern indistinguishable from the original dal⁺ plasmid). These dal⁻ plasmids could not complement the chromosomal dal-1 mutation as an indication that the chromosomal mutation had been transferred to the dal⁻ plasmids by homologous recombination.

3: By Southern blotting analysis of chromosomal *B. subtilis* DNA, it was demonstrated that a chromosomal Cla1-Sph1 fragment hybridized with a fragment of the same size from pDN1000. Thus, no major rearrangement of the dal gene had occurred prior to its cloning on pDN1000.

EXAMPLE 4

Figure 4:
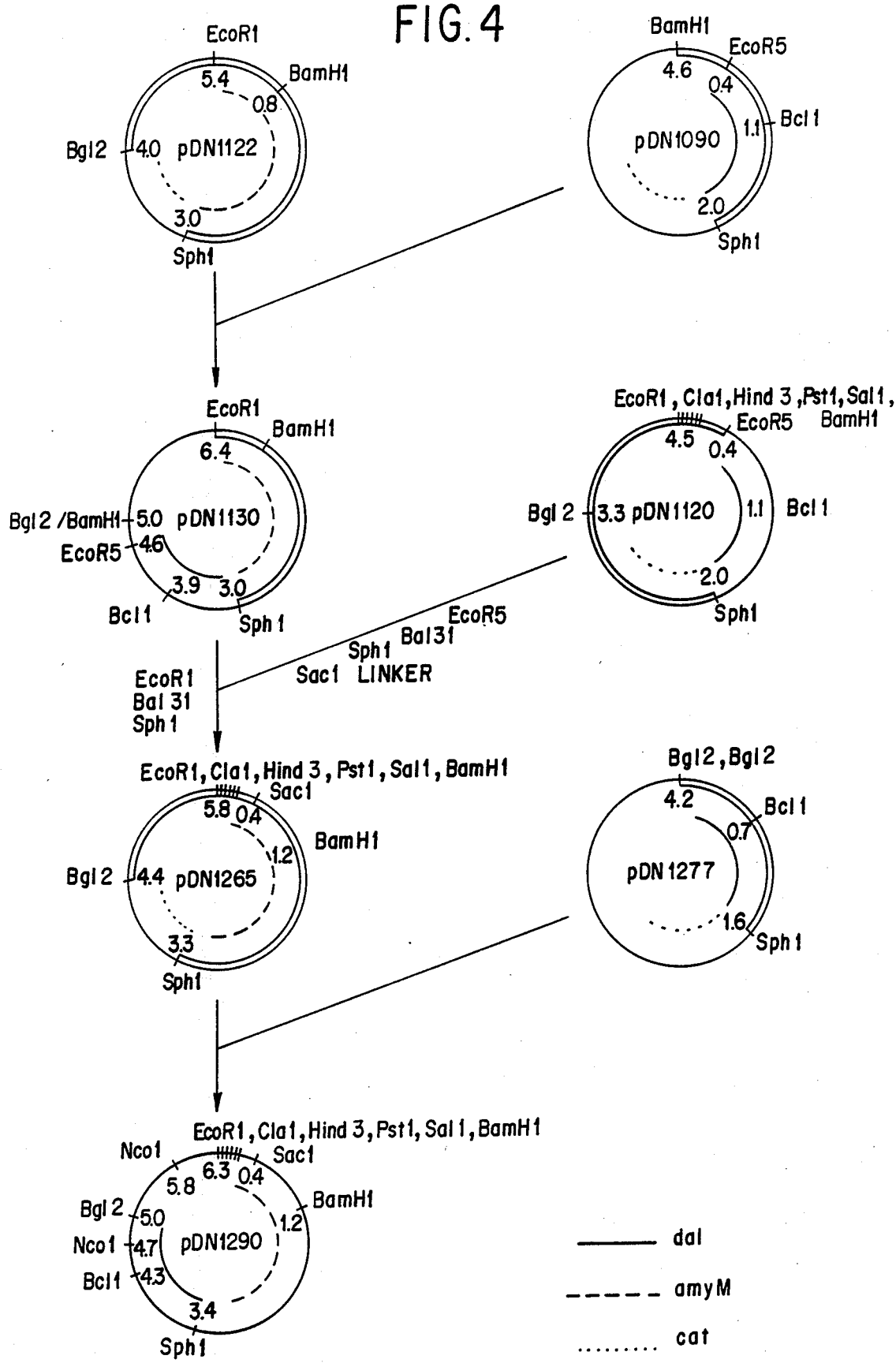
FIG. 4 illustrates the construction of plasmids pDN1130 and pDN1290.

Construction of plasmid pDN1130 (FIGS. 3 and 4)

pDN1000 (from Example 3) harbouring the dal⁺ gene was opened at the Cla1 site, exonuclease digested with Ba131 and ligated with a BamH1 oligonucleotide linker (No. 1017 from Biolabs). The resulting plasmid pDN1090 harbours the dal⁺ gene and confers resistance to chloramphenicol.

pDN1122 (from Example 2) was cut with Sph1 and Bgl2 and a 4.4 kb fragment was ligated with a 2.0 kb Sph1-BamH1 fragment of pDN1090.

The resulting plasmid pDN1130 harbours the amyM⁺ and the dal⁺ gene but does not confer resistance to chloramphenicol.

EXAMPLE 5

Construction of plasmid pDN1290 (FIGS. 3 and 4)

A plasmid pDN1110 dal⁺$Cam^R$ of 4.5 kb was constructed by exonuclease Ba131 digestion of pDN1000 digested with Sph1 and insertion of both a Bgl2 and a Sac1 oligonucleotide linker (No. 1001 and No. 1005 from Biolabs, respectively).

pDN1110 was opened at the single EcoR5 site, exonuclease digested with Ba131 and ligated with two Bgl2 oligonucleotide linkers (No. 1001 from Biolabs). The fusion of linker with one plasmid end created a Bcl1 site. The resulting plasmid pDN1222 harbours the dal⁺ gene and confers resistance to chloramphenicol.

A 0.7 kb Bcl1-Bcl1 fragment of pDN1222 was ligated with a 3.5 kb BamHI-Bcl1 fragment of pDN1090 (from example 4). The resulting plasmid pDN1277 of 4.2 kb harbours the dal⁺ gene and confers resistance to chloramphenicol. Plasmid pDN1277 was transformed into strain DN1280 (see example 6) and the resulting strain DN1517 (=DN1280 pDN1277) was deposited with the National Collection of Industrial Bacteria, Torry Research Station, Aberdeen, Scotland, on December 7, 1984 and accorded the reference number NCIB 12030.

pDN1090 was converted into plasmid pDN1120 dal⁺ $Cam^R$ of 4.5 kb by replacement of a 2.6 kb Sph1-BamH1 fragment with a 2.5 kb Sph1-BamH1 fragment from pDN1050 (prepared as described in example 1).

pDN1265 amyM⁺ $Cam^R$ was constructed by Ba131 exonuclease digestion of pDN1120 digested with EcoR5 and subsequent digestion with Sph1. A fragment of 2.9 kb was then ligated with Sac1 oligonucleotide linker (Biolabs No. 1005) and a 2.9 kb fragment of pDN1130 obtained by digestion with EcoR1 and Ba131 exonuclease treatment, and subsequent digestion with Sph1.

The resulting plasmid pDN1265 of 5.8 kb harbours the amyM⁺ gene and confers resistance to chloramphenicol.

pDN1265 was then cut with Sph1-Bgl2 and a 4.7 kb fragment was ligated with a 1.6 kb Sph1-Bgl2 fragment of pDN1277.

The resulting plasmid pDN1290 of about 6.3 kb harbours the amyM⁺ and the dal⁺ gene but no antibiotic resistance marker.

EXAMPLE 6

Figure 5:
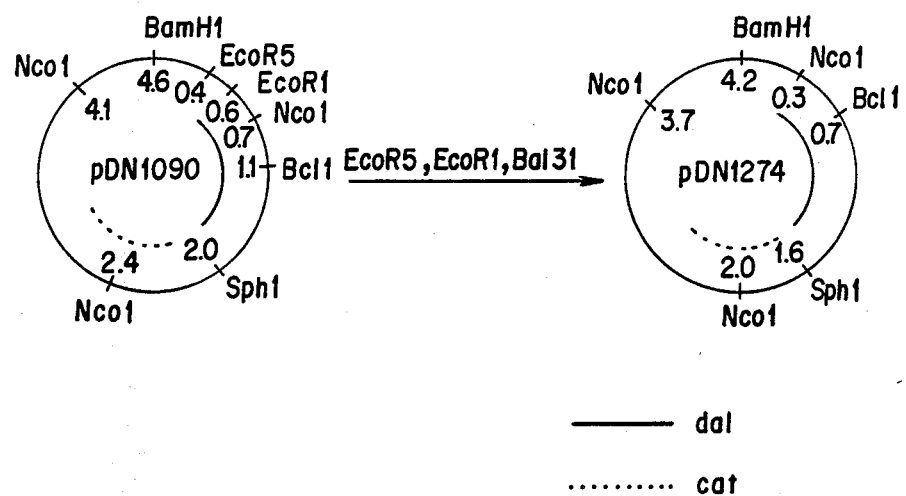
FIG. 5 illustrates the construction of plasmid pDN1274.

Construction of a host with deletion in the dal gene (FIG. 5)

By cutting 5 ug of pDN1090 in the cloned dal⁺ gene with restriction enzymes EcoR1 and EcoR5 and subsequently digesting the fragments with exonuclease Ba131 for 60 sec. ligating and transforming into DN608:dal-1, deletions were obtained which destroyed the Dal⁺ phenotype of the plasmid. Transformation of strain DN497 with one of these deletion plasmids pDN1274 $Cam^R$ dal⁻, and selecting for $Cam^R$ gave about 0.1% of the transformants which were Dal⁻, presumably due to replacement of the chromosomal dal⁺ gene with the dal⁻ deletion from pDN1274. After spontaneously having lost pDN1274, the transformant became $Cam^R$ but remained Dal⁻. Southern blotting analysis of chromosomal DNA of this strain, DN1280, showed that it indeed harboured the expected dal deletion. The frequency of mutations which might cause reversion of this dal deletion mutant to a Dal⁺ phenotype was less than $10^{-8}$. DN1280 harbouring plasmid pDN1277 =DN1517 (see example 5) was deposited.

EXAMPLE 7

Stability of dal⁺ amyM⁺ plasmids in a dal⁻ host

To demonstrate both the stability of the host-plasmid combination DN1300 (=DN1280 pDN1290) and the importance of the absence of overlapping chromosomal and plasmid DNA segments flanking the chromosomal deletion, the following experiment was undertaken:

Single colonies of strains DN1297 (=DN1280 pDN1130) and DN1300 (=DN1280 pDN1290) were resuspended in L-broth supplemented with 10 mM potassium phosphate buffer pH =7.0 and 0.2% glucose. Half of each resuspension was inoculated into the above medium, the other half into an identical medium supplemented with 200 ug/ml D-alanine. By diluting the cultures either 100 or 1000 fold, the strains were grown for a number of generations at 37° C. with good aeration either in the presence or absence of D-alanine in the medium. For each dilution, not less than 10⁷ cells were transferred. With intervals of 1 day, the frequency of Amy⁺ colonies (a total of about 100) were tested on L-broth plates with or without D-alanine according to the growth conditions. The results are shown in Table 1. 10 randomly chosen Amy⁻ colonies were shown not to contain any plasmid.

TABLE 1

Frequency of Amy⁻ Cells After Growth in LB Medium With or Without D-Alanine.

| Strains | Plasmid | Generations 51 | 68 | 85 |
|---|---|---|---|---|
| | | % Amy⁻ | | |
| DN1297 | pDN1130 | 2% | 20% | — |
| DN1297 + D-ala[1] | pDN1130 | 60% | — | — |
| DN1300 | pDN1290 | 0% | 0% | 0% |
| DN1300 + D-ala[1] | pDN1290 | 60% | 90% | — |

[1]First 20 generations in the absence of D-alanine.

The results in Table 1 demonstrate that plasmid pDN1290 is highly unstable during unselective conditions (addition of D-alanine to the growth medium) but becomes stable during growth in a selective medium (without addition of a D-alanine). It is furthermore demonstrated that homologous double crossover restoring the dal+ gene on the host chromosome and subsequent plasmid loss did not take place in DN1300 (no Amy⁻ cells after growth for 85 generations) whereas the frequency of Amy⁻ cells was 20% after 68 generations of DN1297 grown in a D-alanine free medium presumably due to transfer of the dal+ gene from plasmid to chromosome and subsequent plasmid loss.

EXAMPLE 8

Figure 6:
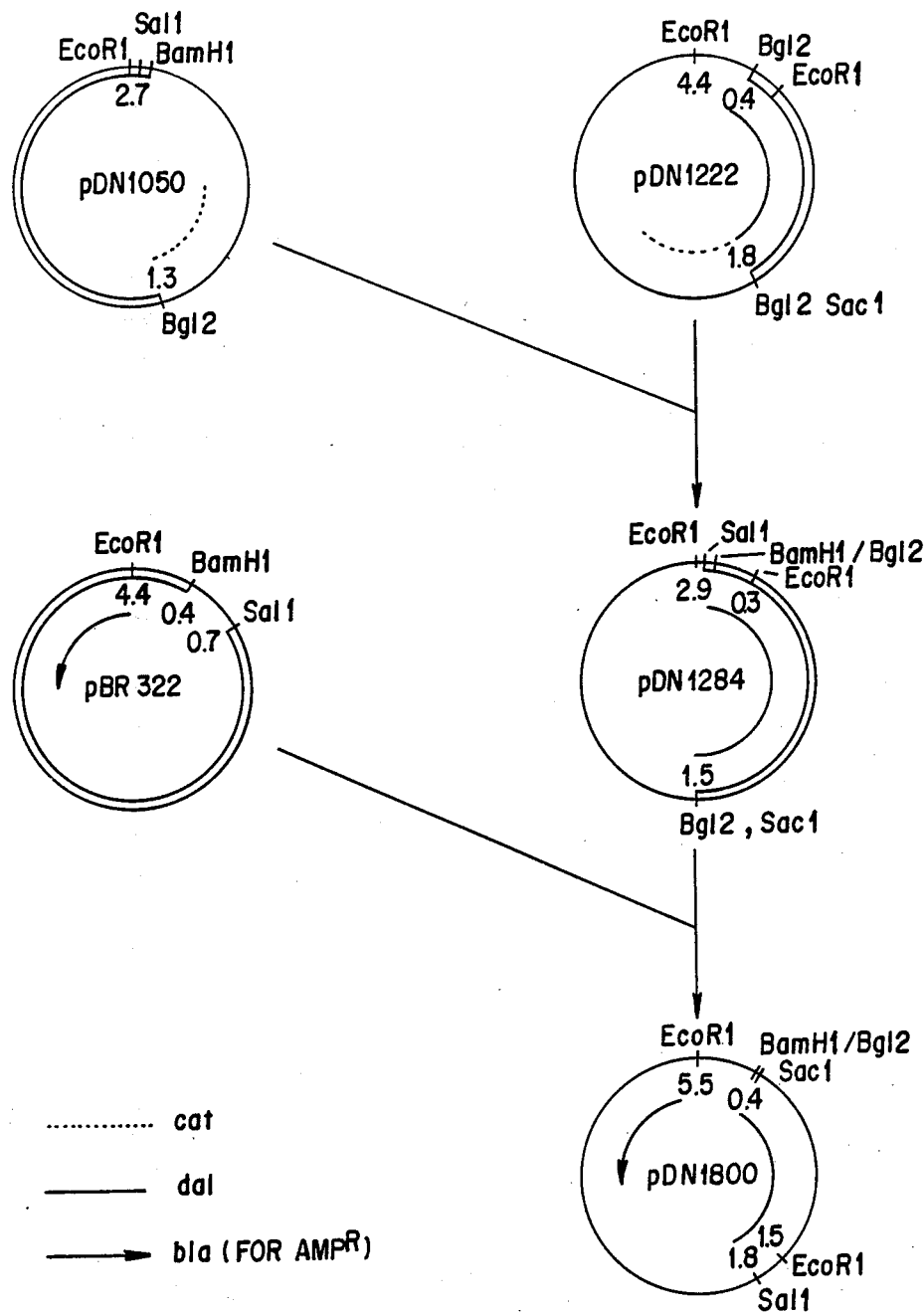
FIG. 6 illustrates the construction of plasmid pDN1800.

Construction of plasmid pDN1800 (FIG. 6)

PDN1284 was constructed by combining the 1.4 kb Bgl2-Bgl2 fragment of pDN1222 (see FIG. 3) with the 1.5 kb BamH1-Bgl2 fragment of pDN1050 (see FIG. 3).

From pDN1284, the dal+ gene was transferred on a 1.4 kb Bgl2-Sall fragment to the classical E. coli plasmid vector pBR322 which had been cut with BamH1 and Sal1. The recombinant plasmid, pDN1800:Amp^R (ampicillin resistant) was transformed into E. coli strain TKL10 selecting for Amp^R to obtain strain DN1800: pDN1800. Strain DN 1800 was deposited with the NCIB on (Nov., 22, 1985, and accorded the reference number NCIB 12181. Accordingly permanence of the deposit and accessability thereto by the public is ensured (vide supra). TKL10 displays a D-alanine requiring phenotype at 42° C. but in DN1800 this requirement is suppressed. Hence, pDN1800 harbouring the dal gene of B. subtilis is able to complement a D-alanine requirement in a E. coli strain defective in alanine racemase activity (Wild et al., *Molec.Gen.Genet.* 198:315-22, 1985).

I claim:

1. A method to obtain stable maintenance of plasmids or bacteriophages in Bacillus or Escherichia bacteria during cultivation comprising:
   (a) inserting a capable of expressing active D,L-alanine racemase in a bacteriophage;
   (b) transforming a bacterial host cell selected from the group consisting of Bacillus and Escherichia, said bacterial host cell having a defect in the chromosomal dal gene encoding D,L-alanine racemase, with said plasmid or bacteriophage; and
   (c) cultivating the transformed bacterial host cell of step (b), wherein the D-alanine requirement of said transformed bacterial host cell caused by its chromosal gene defect is complemented by the dal gene contained in said plasmid or bacteriophage.

2. The method of claim 1, wherein said Bacillus is *Bacillus subtilis*.

3. The method of claim 1, wherein said Escherichia is *Escherichia coli*.

4. The method of claim 1, wherein said bacterial host cell harbors a mutation in dal, the gene encoding D,L-alanine racemase, or a deletion comprising at least part of the dal gene.

5. The method of claim 4, wherein said mutation is a deletion of both a part of the gal gene necessary for expression of the Dal+ phenotype, and a part of directly flanking DNA unnecessary for expression of the Dal+ phenotype.

6. A transformed Bacillus sp. comprising a host Bacillus sp. having a defect in the chromosomal dal gene and further comprising a plasmid or bacteriophage, said plasmid or bacteriophage carrying a DNA fragment comprising the dal+ allele isolated from Bacillus which encodes D,L-alanine racemase wherein said dal+ allele complements the requirement for D-alanine during cultivation of said host.

7. The transformed Bacillus sp. of claim 6, wherein homologous crossover of the dal+ allele from plasmid to chromosome is prevented by insufficient DNA homology.

8. The transformed Bacillus sp. of claim 6, wherein homologous crossover of the dal+ allele from plasmid to chromosome is prevented by a recombination deficiency.

9. The transformed Bacillus sp. of claim 6, wherein said defect in the chromosomal dal gene comprises a deletion of both a part of the dal gene necessary for expression of the Dal+ phenotype and a part of the directly flanking DNA unnecessary for expression of the Dal+ phenotype.

10. A method for the production of a protein or polypeptide in transformed Bacillus or Escherichia bacteria which comprises:
   (a) inserting a dal gene capable of expressing active D,L-alanine racemase bacteriophage wherein said palsmid or bacteriophage also contains a gene for a protein or polypeptide to be produced;
   (b) transforming a bacterial host cell selected from the group consisting of Bacillus and Escherichia, said bacterial host cell having a defect in the chromosomal dal gene for D,L-alanine racemase, with said plasmid or bacteriophage;
   (c) culturing the transformed bacterial host cell of step (b) in a nutrient medium wherein the D-alanine requirement of said transformed bacterial host cell caused by its chromosomal gene defect is complemented by the dal gene contained in said plasmid or bacteriophage, and under conditions wherein said protein or polypeptide is produced; and
   (d) recovering said protein or polypeptide produced in step.(c).

* * * * *

UNITED STATES PATENT AND TRADEMARK OFFICE
CERTIFICATE OF CORRECTION

PATENT NO. : 4,920,048
DATED : April 24, 1990
INVENTOR(S) : Borge K. Diderichsen It is certified that error appears in the above-identified patent and that said Letters Patent is hereby corrected as shown below:

Column 6, line 30, "dalt" should be --$dal^+$--; line 63, "$Dal^{30}$" should be --$Dal^+$--.

Column 7, line 12, "$Amy^-$" should be --$Amy^+$--; line 65, "lacrl" should be --lacyl--.

Column 8, line 48, "aliquotes" should be --aliquots--.

Column 10, line 45, "$Kan^R$ Among" should be --$Kan^R$. Among--; line 51, "$Dal^+Dal^+$" should be --$Dal^+$. $Dal^+$--.

Column 12, line 62, "107" should be --$10^7$--.

Column 13, line 53, "(a) inserting a capable" should be --(a) inserting a dal gene capable--.

Column 14, line 13, "gal" should be --dal--.

Signed and Sealed this

Twenty-eighth Day of April, 1992

Attest:

HARRY F. MANBECK, JR.

*Attesting Officer*          *Commissioner of Patents and Trademarks*